(12) United States Patent
Wang et al.

(10) Patent No.: US 12,054,680 B2
(45) Date of Patent: Aug. 6, 2024

(54) METHOD FOR PRODUCING LIGHT AROMATIC

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Di Wang, Beijing (CN); Xiaoli Wei, Beijing (CN); Jianhong Gong, Beijing (CN); Jingchuan Yu, Beijing (CN); Jiushun Zhang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 198 days.

(21) Appl. No.: 17/755,033

(22) PCT Filed: Aug. 4, 2020

(86) PCT No.: PCT/CN2020/106771
§ 371 (c)(1),
(2) Date: Apr. 19, 2022

(87) PCT Pub. No.: WO2021/082579
PCT Pub. Date: May 6, 2021

(65) Prior Publication Data
US 2022/0389336 A1    Dec. 8, 2022

(30) Foreign Application Priority Data
Oct. 30, 2019  (CN) .......................... 201911047207.3

(51) Int. Cl.
*C10G 67/02* (2006.01)
*B01D 3/14* (2006.01)
(Continued)

(52) U.S. Cl.
CPC ............. *C10G 67/02* (2013.01); *B01D 3/143* (2013.01); *B01D 19/0068* (2013.01);
(Continued)

(58) Field of Classification Search
CPC .............. C10G 67/02; C10G 2300/301; C10G 2300/4006; C10G 2300/4012;
(Continued)

(56) References Cited

U.S. PATENT DOCUMENTS 4,954,326 A     9/1990  Onodera et al.
2016/0102031 A1*  4/2016  Du .......................... C10G 3/57
                                                                585/323

FOREIGN PATENT DOCUMENTS

CN      1217370 A    5/1999
CN      1752058 A    3/2006
(Continued)

OTHER PUBLICATIONS

Iwasa, Yasuyuki et al.; "(Non-official translation)FCA Process Development"; ENEOS Technical Review; vol. 57, No. 1; Feb. 2015; pp. 25-28.

*Primary Examiner* — Randy Boyer
*Assistant Examiner* — Juan C Valencia
(74) *Attorney, Agent, or Firm* — NKL Law; Allen Xue

(57) ABSTRACT

A method for producing light aromatics, includes the steps of: i) contacting a feedstock comprising heavy aromatic(s) with a catalyst in a fluidized reactor for aromatics lightening reaction in the presence of hydrogen to obtain a product rich in C6-C8 light aromatic(s) and a spent catalyst, wherein the heavy aromatic is one or more selected from C9+ aromatics;
(Continued)

ii) separating the resulted product rich in C6-C8 light aromatic(s) to obtain hydrogen, a non-aromatic component, C6-C8 light aromatic(s) and a C9+ aromatic component; and
iii) recycling at least a part of the C9+ aromatic component to the fluidized reactor. The method has strong adaptability to feedstocks and high flexibility in operation and allows a long-period stable operation. The method can produce high-value light aromatics from heavy aromatics that are difficult to be treated and utilized.

20 Claims, 2 Drawing Sheets

(51) Int. Cl.
*B01D 19/00* (2006.01)
*B01J 29/08* (2006.01)
*B01J 29/40* (2006.01)
*B01J 29/90* (2006.01)

(52) U.S. Cl.
CPC ............ *B01J 29/084* (2013.01); *B01J 29/40* (2013.01); *B01J 29/90* (2013.01); *C10G 2300/301* (2013.01); *C10G 2300/4006* (2013.01); *C10G 2300/4012* (2013.01); *C10G 2300/4018* (2013.01); *C10G 2300/708* (2013.01); *C10G 2400/30* (2013.01)

(58) Field of Classification Search
CPC ...... C10G 2300/4018; C10G 2300/708; C10G 2400/30; C10G 69/02; C10G 45/64; C10G 47/30; C10G 2300/1096; C10G 45/66; C10G 47/20; C10G 67/04; C10G 67/14; C10G 2300/1037; C10G 2300/104; C10G 2300/1044; C10G 2300/70; B01D 3/143; B01D 19/0068; B01J 29/084; B01J 29/40; B01J 29/90; B01J 29/46; B01J 29/126; B01J 29/146; B01J 29/44; B01J 2229/20; B01J 29/80; B01J 2229/42; B01J 37/0045; B01J 38/30; Y02P 20/52; C07C 4/12; C07C 6/12; C07C 15/02; C07C 15/04; C07C 15/06; C07C 15/08; C07C 6/126

See application file for complete search history.

(56) References Cited

FOREIGN PATENT DOCUMENTS

| | | | |
|---|---|---|---|
| CN | 1906272 A | 1/2007 | |
| CN | 1918089 A | 2/2007 | |
| CN | 101045668 A | 10/2007 | |
| CN | 101348405 A | 1/2009 | |
| CN | 101348733 A | 1/2009 | |
| CN | 101607207 A | 12/2009 | |
| CN | 101734986 A | 6/2010 | |
| CN | 103930524 A | 7/2014 | |
| CN | 107759430 A | 3/2018 | |
| CN | 109705910 A | 5/2019 | |
| CN | 109718760 A | 5/2019 | |
| CN | 109952152 A | 6/2019 | |
| CN | 110075911 A | 8/2019 | |
| EP | 0731071 A1 | 9/1996 | |
| JP | 2007526301 A | 9/2007 | |
| JP | 2012240998 A | 12/2012 | |
| JP | 2018158282 A | 10/2018 | |
| WO | WO-2007027435 A2 * | 3/2007 | ........... C07C 5/2708 |
| WO | 2013169465 A1 | 11/2013 | |
| WO | WO-2018071184 A1 * | 4/2018 | ............ B01J 29/068 |

* cited by examiner

METHOD FOR PRODUCING LIGHT AROMATIC

CROSS REFERENCE TO RELATED APPLICATIONS

This application is a U.S. national entry of PCT International Application No. PCT/CN2020/106771, filed on Aug. 4, 2020, which claims priority from Chinese patent application No. 201911047207.3, titled "method for producing light aromatic", filed on Oct. 30, 2019, the contents of which are incorporated herein by reference in their entirety.

TECHNICAL FIELD

The present application relates to a method for producing light aromatics, particularly to a method for producing light aromatics from a feedstock comprising heavy aromatic(s).

BACKGROUND ART

BTX (benzene, toluene and xylene) is an important petrochemical basic product and an important starting material for various chemical products such as synthetic rubber, synthetic fiber and synthetic resin, and the toluene and xylene can also be used as an additive for improving the octane number of gasoline. Due to the continuous developing of terylene, polyester and PTA industries in China, the growth of global aromatic hydrocarbon industrial chain is concentrated in northeast Asia regions, and the demand of BTX is continuously increased. However, aromatics production processes are accompanied by the production of C9+ heavy aromatics, and current production of C9+ heavy aromatics with low value and limited utilization is very large, which causes a waste of resources. Thus, the conversion of C9+ heavy aromatics in the catalytic cracking gasoline into BTX, with a co-production of more light olefins, is undoubtedly an effective way for fully utilizing resources and improving the quality and efficiency of enterprises.

CN1217370A discloses a process for hydrodealkylation and transalkylation of heavy aromatics, in which C10 or/and C11 aromatics are used as a feedstock, a hydrogen-type mordenite loaded with bismuth and at least one metal selected from iron, cobalt, nickel or molybdenum or an oxide thereof is used as a catalyst, and the reaction is carried out in a fixed bed reactor at a temperature of 300-600° C. and a pressure of 1.5-4.0 MPa to produce C6-C9 aromatics and C1-C4 paraffins. The process is particularly suitable for hydrodealkylation and transalkylation of C10+ heavy aromatics, and can be used in industrial production.

CN101362669A discloses a catalytic conversion method for preparing ethylene, propylene and aromatics, characterized in that comprising the steps of contacting hydrocarbon feedstocks with different cracking behaviors with a catalytic cracking catalyst to conduct a cracking reaction in a fluidized bed reactor, separating the spent catalyst and reaction oil gas, recycling the spent catalyst to the reactor after regeneration, and separating the reaction oil gas to obtain the target products, namely light olefin and aromatics, wherein a fraction of 160-260° C. is recycled to the catalytic cracking for reuse, and ethane, propane and butane are subjected to steam cracking to further produce ethylene and propylene. The method is capable of producing light olefins such as ethylene, propylene and the like from heavy feedstocks to the maximum extent, with a co-production of aromatics such as toluene, xylene and the like, thereby the yields of ethylene and propylene can both be more than 20 wt %.

CN1752058A discloses a method for hydrodealkylation and transalkylation of heavy aromatics, which mainly aims at solving the problems in the prior art, that is a low allowable content of heavy aromatics in feedstocks and a utilization rate of heavy aromatics. The method solves the above problems by conducting a reaction in a fixed bed reactor at a temperature of 300-600° C. and a pressure of 1.0-4.0 MPa using C10 or/and C11 aromatics as feedstock, and a macroporous zeolite loaded with metallic bismuth and molybdenum or oxides thereof as catalyst, to produce mixed xylene. The method has the characteristics of simple process, high yield of mixed xylene, low hydrogen-hydrocarbon ratio and the like, and can be used for industrial production of mixed xylene from heavy aromatics.

CN1906272A discloses a process for the separate catalytic hydrodealkylation of hydrocarbons comprising C8-C13 alkyl-aromatics optionally mixed with C4-C9 aliphatic and cycloaliphatic products, which process comprises continuously treating the hydrocarbon composition with a catalyst consisting of ZSM-5 zeolite and modified with at least one metal selected from Group IIB, Group VIB, and Group VIII metals, in the presence of hydrogen, at a temperature of 400-650° C., a pressure of 2-4 MPa, and a Hz/feedstock molar ratio of 3-6. The process can provide a total yield of benzene and toluene up to 75%.

CN101348733A discloses a process for producing light aromatics and light paraffins from hydrocarbon feedstocks, comprising the steps of reacting a hydrocarbon feedstock with a boiling point of 30-250° C. in the presence of a zeolite catalyst comprising Pt or Pd, subjecting heavy aromatics in the hydrocarbon feedstock to hydrodealkylation and to transalkylation reaction with light aromatics, subjecting the light aromatics to isomerization reaction to convert them into a component rich in BTX (B is benzene, T is toluene, and X is xylene) light aromatics, subjecting non-aromatics to hydrocracking reaction to generate light paraffins, separating liquid products into benzene, toluene, xylene, and C9+ aromatics according to the difference in boiling points in a distillation column, and separating the light paraffins from gas products. The process solves the problems encountered in traditional separation processes for hydrocarbon feedstocks, e.g. the requirement of solvent extraction, complexity in process, high cost, and low value of heavy aromatics and non-aromatics obtained after separation.

CN101734986A discloses a process for producing more benzene and xylene by hydrocracking of cracking gasoline. The process comprises reacting a C7+ cracking gasoline feedstock in the presence of a catalyst, subjecting heavy aromatics to hydrodealkylation and to transalkylation reaction with light aromatics, subjecting the light aromatics to isomerization reaction to convert them into a component rich in BTX light aromatics, separating liquid products into benzene, toluene, xylene and a C9+ fraction according to the difference in boiling points, wherein the toluene and the C9+ fraction can be recycled for further treatment, and separating the light paraffins from gas products. The process solves the problems encountered in traditional processes for treating cracking gasoline, that is only a separation of BTX (B is benzene, T is toluene and X is xylene) aromatics is conducted, the light aromatic product comprises a large amount of toluene, and the value of the separated heavy aromatics and non-aromatics is low.

CN103930524A discloses a process for converting a biomass into products, comprising the steps of contacting the biomass with hydrogen in the presence of a hydropyrolysis catalyst in a fluidized bed reaction vessel under hydropyrolysis conditions; and removing the product and carbon from the reaction vessel, wherein the carbon and the catalyst are separated according to the difference in settling velocities.

The technology disclosed in the above patent applications shows that existing heavy aromatics lightening technologies mostly adopt a fixed bed hydrodealkylation process, and have the disadvantages of harsh reaction conditions, difficulty in catalyst regeneration and recycling, and strict requirement on initial activity of catalysts.

SUMMARY OF THE INVENTION

An object of the present application is to provide a method for producing light aromatics, which can efficiently convert C9+ heavy aromatics into C6-C8 light aromatics and allow a long-period stable operation.

To achieve the above object, the present application provides a method for producing light aromatics, comprising the steps of:
  i) contacting a feedstock comprising heavy aromatic(s) with a catalyst in a fluidized reactor for aromatics lightening reaction in the presence of hydrogen to obtain a product rich in C6-C8 light aromatic(s) and a spent catalyst, wherein the heavy aromatic is one or more selected from C9+ aromatics;
  ii) separating the resulted product rich in C6-C8 light aromatic(s) to obtain hydrogen, a non-aromatic component, C6-C8 light aromatic(s) and a C9+ aromatic component; and
  iii) recycling at least a part of the C9+ aromatic component to the fluidized reactor,
wherein:
  the reaction conditions of step i) include: a temperature of about 250-750° C., a pressure of about 0-6 MPa, a weight hourly space velocity of about 0.1-120 h$^{-1}$, and a hydrogen/hydrocarbon molar ratio of about 1-15,
  the catalyst used in step i) comprises a carrier and an active metal component supported on the carrier in an amount of about 0.01-50 wt %, based on the total weight of the catalyst,
  wherein the carrier comprises from about 1 to about 80 wt % of zeolite, from about 5 to about 99 wt % of inorganic oxide, and from about 0 to about 70 wt % of clay, based on the total weight of the carrier, wherein the zeolite comprises a mesoporous zeolite, a macroporous zeolite, or a combination thereof; the inorganic oxide is one or more selected from silica, alumina, zirconia, titania and amorphous silica-alumina; the clay is one or more selected from kaolin, montmorillonite, diatomite, attapulgite, sepiolite, halloysite, hydrotalcite, bentonite and rectorite,
  the active metal component is one or more selected from rare earth metals and transition metals.

The method according to the present application employs a fluidized reaction system to carry out hydrodealkylation and transalkylation treatment on the feedstock comprising C9+ heavy aromatics, which has strong feedstock adaptability and high flexibility in operation, allows a long-period stable operation, and can convert heavy aromatics that are difficult to treat and utilize into light aromatics with high value.

Additional features and advantages of the present application will be described in detail in the Detailed Description hereinbelow.

BRIEF DESCRIPTION OF THE DRAWINGS

The drawings, forming a part of the present description, are provided to help the understanding of the present application, and should not be considered to be limiting. The present application can be interpreted with reference to the drawings in combination with the Detailed Description hereinbelow. In the drawings.

DETAILED DESCRIPTION OF THE INVENTION

Figure 1:
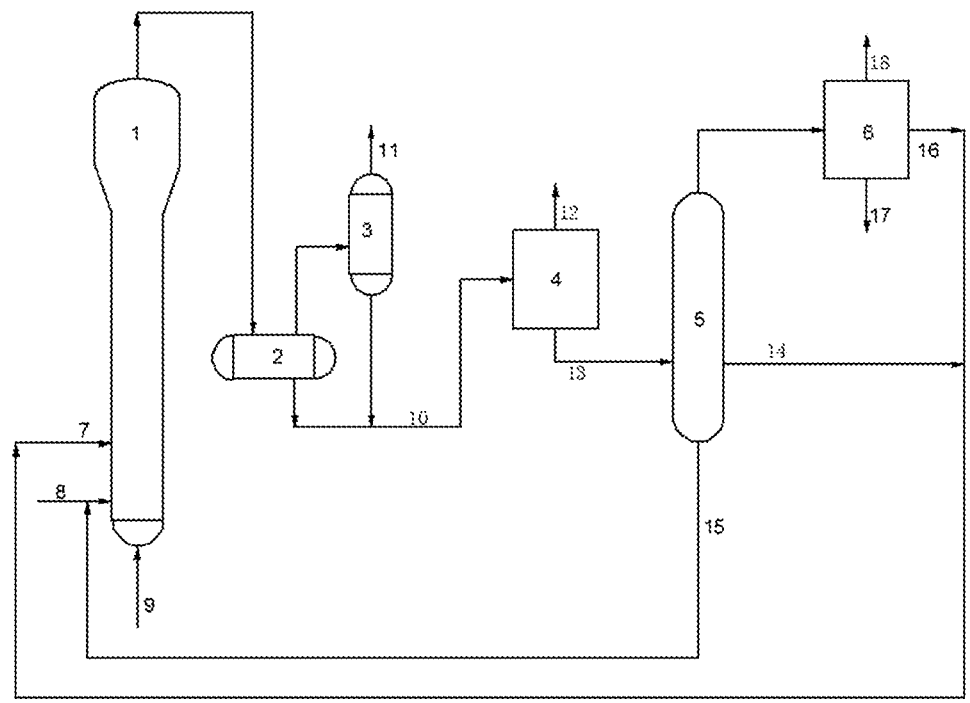
FIG. 1 shows a process flow diagram of an embodiment of the method according to the present application.

The present application will be further described hereinafter in detail with reference to specific embodiments thereof and the accompanying drawings. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value, such as any possible value within ±5% of the exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by those skilled in the art; and if the terms are defined herein and their definitions are different from the ordinary understanding in the art, the definition provided herein shall prevail.

In the present application, the term "C9+ aromatics" is a generic term for aromatic compounds having 9 or more carbon atoms, which is intended to cover any existing aromatic compound having 9 or more than 9 carbon atoms. Similarly, in the present application, the term "C10+ aromatics" is a generic term for aromatic compounds having 10 or more carbon atoms and is intended to cover any existing aromatic compound having 10 or more than 10 carbon atoms.

In the present application, the term "C6-C8 light aromatics" is a generic term for aromatic compounds having 6-8 carbon atoms, which is intended to cover any existing aromatic compound having 6, 7, or 8 carbon atoms.

In the present application, the terms "fluidized reactor" and "fluidized bed reactor" are used interchangeably, and refer to a reactor in which solid catalyst particles are brought into a state of suspension flow by a gaseous process stream to conduct a gas-solid reaction process, which include various forms of dilute-phase conveying beds, dense-phase conveying beds, bubbling fluidized beds, turbulent fluidized beds, fast fluidized beds, and the like.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to those skilled in the art that such a combination is obviously unreasonable.

All of the patent and non-patent documents cited herein, including but not limited to textbooks and journal articles, are hereby incorporated by reference in their entirety.

The present application provides a method for producing light aromatics, comprising the steps of:
  i) contacting a feedstock comprising heavy aromatic(s) with a catalyst in a fluidized reactor for reaction in the presence of hydrogen under effective conditions for converting heavy aromatic(s) into light aromatic(s), to obtain a product rich in C6-C8 light aromatic(s) and a spent catalyst, wherein the heavy aromatic is one or more selected from C9+ aromatics;
  ii) separating the resulted product rich in C6-C8 light aromatic(s) to obtain hydrogen, a non-aromatic component, C6-C8 light aromatic(s) and a C9+ aromatic component; and
  iii) recycling at least a part of the C9+ aromatic component to the fluidized reactor.

The method according to the present application employs a fluidized reaction system, so that the feedstock and catalyst can continuously react in the fluidized reactor, and thus has strong feedstock adaptability and high flexibility in operation, and allows a long-period stable operation.

The method according to the present application can relieve the contradiction between supply and demand of light aromatics, solve the problem of high production of heavy aromatics with low value and difficulty in utilization encountered by various oil refining and chemical engineering processes, and improve the economic benefit and social benefit of petrochemical industry.

According to the present application, in step i), the C9+ heavy aromatic(s) may undergo dealkylation and transalkylation reactions to obtain C6-C8 light aromatic(s). The reaction conditions in step i) may vary within wide limits. In a preferred embodiment, the reaction temperature may be about 250-750° C., preferably about 320-600° C., more preferably about 360-550° C., such as about 380-500° C. or about 400-480° C.; the pressure (gauge pressure) may be from about 0 to about 6 MPa, preferably from about 0 to about 4.5 MPa, more preferably from about 1 to about 3 MPa; the weight hourly space velocity (e.g., for a dense-phase fluidized bed) may be from about 0.1 to about 120 $h^{-1}$, preferably from about 1 to about 80 $h^{-1}$, more preferably from about 1.5 to about 50 $h^{-1}$, such as from about 1 to about 30 $h^{-1}$, from about 1.5 to about 15 $h^{-1}$, from about 1 to about 10 $h^{-1}$, or from about 1.5 to about 10 $h^{-1}$, or the reaction time (e.g., for a conveying bed reactor) is from about 0.1 to about 40 seconds, preferably from about 0.5 to about 30 seconds, more preferably from about 1 to about 15 seconds, such as from about 0.2 to about 20 seconds, or from about 0.6 to about 10 seconds; and the hydrogen/hydrocarbon molar ratio may be from about 1 to about 15, preferably from about 2 to about 10, more preferably from about 3 to about 8, such as from about 3 to about 5.

According to the present application, after the oil gas obtained from the fluidized reactor is separated from the spent catalyst, a reaction product rich in C6-C8 light aromatic(s) is obtained, and the reaction product can be further separated to obtain hydrogen, a non-aromatic component, C6-C8 light aromatic(s) and a C9+ aromatic component, wherein the separation can be carried out by any method conventionally used in the art. In a preferred embodiment, the product rich in C6-C8 light aromatic(s) can be subjected to gas-liquid separation to obtain hydrogen and a liquid product, and then the liquid product can be subjected to aromatics extraction to obtain a non-aromatic component and an aromatic component. Preferably, the separated hydrogen may be recycled to the fluidized reactor of step i).

In a further preferred embodiment, to separate out the C6-C8 light aromatic(s), the aromatic component may be subjected to a first fractionation to yield C6-C8 light aromatic(s) and a C9+ aromatic component; wherein at least a part of the C9+ aromatic component can be recycled to the fluidized reactor for further reaction, and particularly preferably, the whole C9+ aromatic component can be recycled to the fluidized reactor for further reaction. The device and conditions for carrying out the first fractionation may be those conventionally used in the art, for example the device for the first fractionation may be a fractionation column, or a flash drum and the conditions for the first fractionation may be those conventionally used in the art.

In another further preferred embodiment, the C9 aromatic(s) and the C10+ aromatic component of the C9+ aromatic component may be separated, for example, by carrying out a second fractionation on the aromatic component to yield C6-C8 light aromatic(s), C9 aromatic(s), and C10+ aromatic component. The device and conditions for carrying out the second fractionation may be those conventionally used in the art, for example the device for the second fractionation may be a fractionation column and the conditions for the second fractionation may be those conventionally used in the art.

According to the present application, the C6-C8 light aromatic(s) separated from the product can be sent out of the system as a product, or otherwise be further separated to obtain benzene, toluene and xylene. The method for separation may be those conventionally used in the art, for example, the C6-C8 light aromatic(s) may be subjected to a third fractionation to yield benzene, toluene, and xylenes. The device and conditions for carrying out the third fractionation may be those conventionally used in the art, for example the device for the third fractionation may be a fractionation column and the conditions for the third fractionation may be those conventionally used in the art.

In preferred embodiments where a second fractionation is carried out on the aromatic component, the C9 aromatic(s) separated by the second fractionation may be subjected to transalkylation with toluene to produce more xylenes. In a still further preferred embodiment, as shown in FIG. 1, a mixed recycle feed may be obtained by mixing the C9 aromatic(s) with toluene separated from the C6-C8 light aromatic(s) and recycling the mixed recycle feed to the fluidized reactor. Toluene and the C9 aromatic(s) in the mixed recycle feed may undergo toluene disproportionation and transalkylation with the C9 aromatic(s) in a fluidized reactor to generate xylene, so as to increase the xylene content of the light aromatic product. Also, in this embodiment, the C10+ aromatic component may be mixed with the feedstock comprising heavy aromatic(s) before being recycled to the fluidized reactor for reaction.

Further preferably, to increase the reaction conversion in the fluidized reactor, in a particularly preferred embodiment, as shown in FIG. 1, the C10+ aromatic component and the mixed recycle feed may be sequentially fed into the fluidized reactor along the flow direction of the feedstock in the fluidized reactor, i.e. the C10+ aromatic component may be fed at an upstream position of the fluidized reactor and the mixed recycle feed comprising toluene and C9 aromatic(s) may be recycled to the fluidized reactor downstream of the inlet for the heavy aromatic feedstock. In the reactor shown in FIG. 1, the fluidized reactor is a riser reactor, and the position of the inlet for the mixed recycle feed is higher than the position of the inlet for the feedstock comprising heavy aromatic(s); in embodiments where the fluidized reactor is a downer reactor, the position of the inlet for the mixed recycle feed is lower than the position of the inlet for the feedstock comprising heavy aromatic(s).

According to the present application, the separation of the spent catalyst from the oil gas can be carried out by means of cyclones well known to those skilled in the art, or by means of filters well known to those skilled in the art. The oil gas obtained after the separation of the spent catalyst, namely the reaction product rich in C6-C8 light aromatic(s), can be subjected to a subsequent separation system to separate gases, a non-aromatic component, C6-C8 light aromatic(s) and C9+ aromatic component the is relatively heavier, and further separate desired products such as BTX, and the separation can be carried out by methods conventionally used in the art with no particular limitation in the present application, of which a detail description is omitted herein.

According to the present application, the separated spent catalyst can be sent to a regeneration reactor for regeneration and then recycled, and the product rich in C6-C8 light aromatic(s) can be subjected to gas-liquid separation to separate hydrogen. As shown in FIG. 1, the product rich in C6-C8 light aromatic(s) is passed through a two-stage cooling gas-liquid separator, for example, sequentially sent to a hot product gas-liquid separation tank and a cold product gas-liquid separation tank for separation, and hydrogen is obtained from the top of the cold product gas-liquid separation tank, which can be recycled to the fluidized reactor as recycle hydrogen, and the liquid products obtained from the bottoms of the two gas-liquid separation tanks can be further separated.

In a preferred embodiment of the present application, the spent catalyst may be sent to a fluidized bed regenerator for regeneration and the resulted regenerated catalyst may be recycled to the fluidized reactor. The regeneration of the spent catalyst may be carried out in a manner well known to those skilled in the art, and all or at least part of the catalyst used in step i) may be derived from the regenerated catalyst. In the regeneration process, an oxygen-containing gas, for example air, may typically be introduced into the regenerator from the bottom thereof. After the introduction of the oxygen-containing gas in the regenerator, the spent catalyst is contacted with oxygen for regeneration by coke burning, the flue gas generated from the regeneration of the catalyst is subjected to gas-solid separation in an upper part of the regenerator, and then passed to a subsequent energy recovery system. Depending on the property of the active metal component of the catalyst, regeneration processes like reduction and sulfurization may be incorporated.

Figure 2:
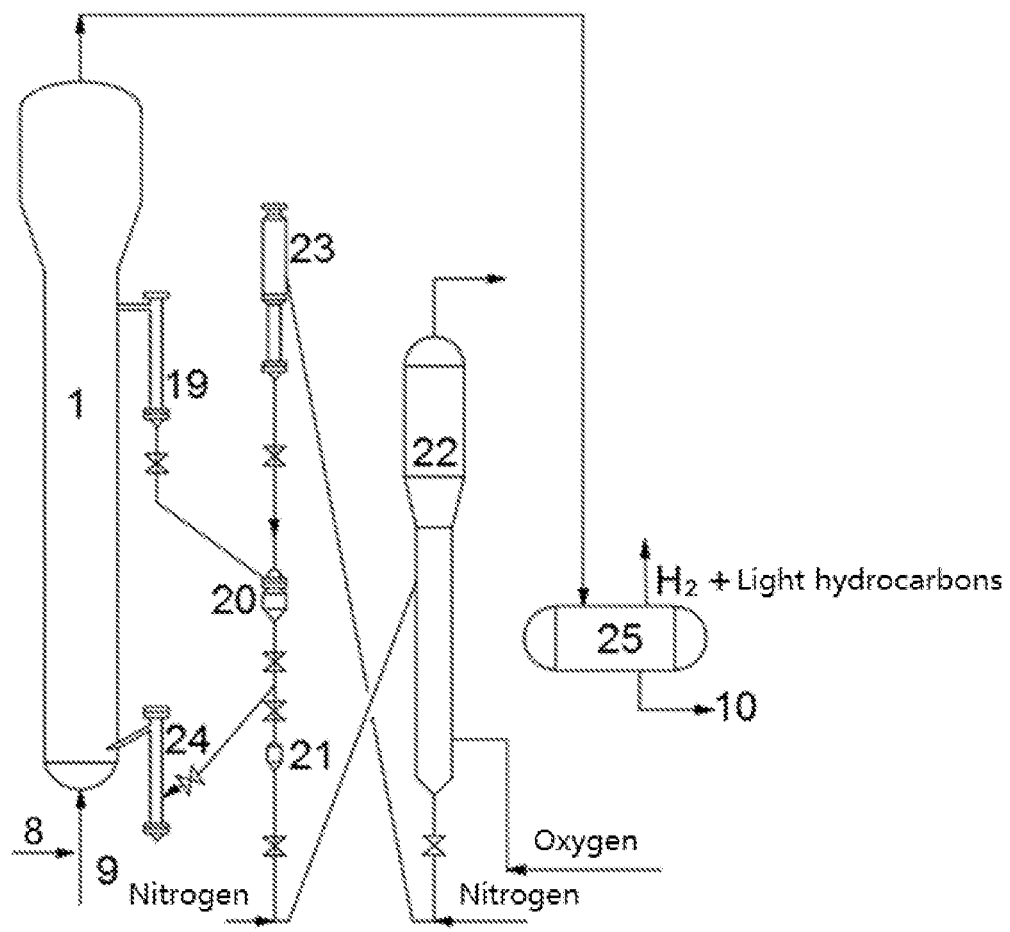
FIG. 2 shows a schematic diagram of a regenerator in accordance with an embodiment of the method according to the present application.

To avoid the contact between hydrogen-containing gas stream with oxygen-containing gas stream during the catalyst regeneration, and to improve plant safety, in a preferred embodiment, as shown in FIG. 2, the fluidized bed regenerator may further comprise a lock hopper, and the regeneration method may comprise: passing the spent dealkylation catalyst through a lock hopper into the fluidized bed regenerator for regeneration and recycling the regenerated dealkylation catalyst to the fluidized reactor through the lock hopper. In this embodiment, the lock hopper allows for safe and efficient transfer of the catalyst from the high pressure hydrocarbon or hydrogen environment in the reactor to the low pressure oxygen environment in the regenerator, and from the low pressure oxygen environment in the regenerator to the high pressure hydrocarbon or hydrogen environment in the reactor. In a preferred embodiment, the method of the present application further comprises the steps of depressurizing the spent catalyst and subsequently pressurizing the regenerated catalyst in the lock hopper.

According to the present application, by using the lock hopper, the reducing atmosphere (hydrogen atmosphere) in the reactor and the feeding tank of the regenerated catalyst can be well isolated from the oxygen-containing atmosphere in the regenerator for coke-burning regeneration, so that the safety of the process and method can be ensured, the operating pressure of the reactor and the regenerator can be flexibly regulated and controlled. Particularly, the operating pressure of the reactor can be increased without increasing the operating pressure of the regenerator, so that the treatment capacity of the plant can be increased. The lock hopper described herein is a device that allows a stream to be switched between different atmospheres (e.g., oxidizing and reducing atmospheres) and/or different pressure environments (e.g., from high pressure to low pressure, or vice versa), the configuration and operation of which are easy to be realized by those skilled in the art based on the disclosure herein.

In a further preferred embodiment, as shown in FIG. 2, the fluidized bed regenerator may further comprise a reactor receiver 19, a regenerator receiver 23, a regenerator feed tank 21, and optionally a reducer 24, and the spent catalyst withdrawn from the fluidized reactor may be transferred to the reactor receiver 19, then to the regenerator feed tank 21 via a lock hopper 20, and then from the regenerator feed tank 21 to the fluidized bed regenerator 22, and subjected to regeneration by coke burning in the regenerator under an oxygen-containing atmosphere to obtain a regenerated dealkylation catalyst; the regenerated catalyst is continuously withdrawn from the fluidized bed regenerator 22, passed to the reducer 24 through the regenerator receiver 23, and recycled to the fluidized reactor for reuse after being reduced. Still further preferably, the spent catalyst may be depressurized in the lock hopper 20 and the regenerated catalyst may be pressurized in the lock hopper 20, if desired.

In other embodiments of the present application, the catalyst transfer between the regenerator and the reactor may be conducted using regenerated catalyst standpipe and spent catalyst standpipe.

According to the present application, the feedstock comprising heavy aromatic(s) comprises at least one C9+ aromatic hydrocarbon, which means the feedstock may be a pure C9+ aromatic hydrocarbon or a feedstock comprising a C9+ aromatic hydrocarbon, preferably a feedstock rich in C9+ aromatic(s); the content of C9+ aromatic(s) in the feedstock comprising heavy aromatic(s) can vary over a wide range, and preferably the content of C9+ aromatic(s) can be in a range of about 20 wt % to about 100 wt %, and more preferably in a range of about 30 wt % to about 100 wt %.

According to the present application, the feedstock comprising heavy aromatic(s) may have an initial boiling point of about 120-150° C., preferably about 130-140° C., a final boiling point of about 200-250° C., preferably about 205-240° C., and a distillation range of about 120-250° C., preferably about 140-220° C.

According to the present application, the feedstock comprising heavy aromatic(s) may be derived from the processes of steam cracking, catalytic cracking, catalytic reforming, PX production and the like, or other processes capable of producing C9+ aromatics, for example, the feedstock meeting the above requirements can be at least one of heavy aromatics derived from steam cracking gasoline, heavy aromatics derived from catalytic cracking gasoline, heavy aromatics derived from catalytic reforming and C9+ heavy aromatics from the bottom of xylene column in aromatics complex unit.

According to the present application, the catalyst used in step i) may comprise a carrier and an active metal component supported on the carrier, and the composition and content of the catalyst may vary over a wide range. In a preferred embodiment, based on the total weight of the catalyst, the carrier may be present in the catalyst in an amount of from about 50 to about 99.99 wt %, preferably from about 55 to about 85 wt %; and the active metal component may be present in an amount of about 0.01 to about 50 wt %, preferably about 0.01 to about 45 wt %.

According to the present application, the active metal component is preferably one or more of rare earth metals and transition metals, such as Fe, Ni, Pt, Pd, Co and Mo, preferably Ni, Pt and Pd. When the active metal component is a noble metal, it is preferably present in an amount of about 0.01 to about 5 wt %; and when the active metal component is a non-noble metal, it is preferably present in an amount of about 0.01 to about 30 wt %, calculated on the basis of metal elements and based on the total weight of the catalyst.

According to the present application, when the active metal component is a noble metal, the dealkylation catalyst does not need to be presulfided; and when the active metal component is a non-noble metal, the catalyst may or may not be presulfided.

According to the present application, the composition and content of the carrier may also vary within a wide range. In a preferred embodiment, the carrier may comprise from about 1 to about 80 wt % of zeolite, from about 5 to about 99 wt % of inorganic oxide, and from about 0 to about 70 wt % of clay, based on the dry weight of the carrier; further preferably, the carrier may comprise about 10 to about 50 wt % of zeolite, about 10 to about 90 wt % of inorganic oxide, and about 1 to about 60 wt % of clay. Preferably, the zeolite may comprise a mesoporous zeolite, a macroporous zeolite, or a combination thereof, preferably selected from the group consisting of mesoporous zeolite, macroporous zeolite, or a combination thereof. Further preferably, based on the total weight of the zeolite, the mesoporous zeolite is present in an amount of from about 0 to about 100 wt %, preferably from about 50 to about 100 wt %, more preferably from about 70 to about 90 wt %; the macroporous zeolite is present in an amount of about 0 to about 100 wt %, preferably about 0 to about 50 wt %, more preferably about 10 to about 30 wt %.

According to the present application, in the carrier of the catalyst, the mesoporous and macroporous zeolites may be of the type conventionally used in the art. For example, the mesoporous zeolite is preferably one or more selected from ZSM zeolites and ZRP zeolites, and the macroporous zeolite is preferably one or more selected from β zeolites, REY zeolites, REHY zeolites, ultrastable Y zeolites and high silica Y zeolites.

According to the present application, in the carrier of the catalyst, the inorganic oxide and the clay may each be of the type conventionally used in the art, for example, the inorganic oxide may be one or more of silica, alumina, zirconia, titania and amorphous silica-alumina, preferably silica and/or alumina; the clay may be one or more selected from kaolin, montmorillonite, diatomite, attapulgite, sepiolite, halloysite, hydrotalcite, bentonite and rectorite, preferably kaolin and/or halloysite.

According to the present application, the carrier may be subjected to hydrothermal aging treatment under the following conditions: a temperature of about 700° C. to about 850° C. and an atmosphere of up to 100% steam, or may be used without hydrothermal aging.

According to the present application, the catalyst is preferably in the form of microspheroidal particles having the following particle size distribution: a mass fraction of particles from 0 to 20 μm of less than about 5%, a mass fraction of particles from 0 to 40 μm of less than about 30%, a mass fraction of particles from 0 to 149 μm of greater than about 80%, and an average particle size of about 50 to about 90 μm, preferably about 60 to about 80 μm; and a catalyst attrition index of less than about 10%/h, preferably less than about 5%/h.

According to the present application, the fluidized reactor is preferably selected from the group consisting of a conveying bed reactor, a dense-phase fluidized bed reactor, a composite reactor composed of a conveying bed reactor and a dense-phase fluidized bed reactor, a composite reactor composed of two or more conveying bed reactors or a composite reactor composed of two or more dense-phase fluidized bed reactors; wherein the conveying bed reactor may be, for example, a riser reactor; and the dense-phase fluidized bed reactor may be, for example, a bubble bed reactor, a turbulent fluidized bed reactor, or the like. In a preferred embodiment, the fluidized reactor used is a dense-phase fluidized-bed reactor which may comprise an expanded segment at an upper part in which cyclones or catalyst filters may be provided for recovering catalyst entrained in the gas stream. When a dense-phase fluidized bed reactor or a riser reactor is used, the feeding and operation mode thereof may be the same as that conventionally adopted in existing dense-phase fluidized bed reactor and riser reactor, and there is no particular limitation in the present application.

In a particularly preferred embodiment, as shown in FIG. 1, the method for producing light aromatics according to the present application is carried out as follows: a feedstock 8 comprising heavy aromatic(s) and hydrogen 9 are separately fed to a fluidized reactor 1 from a lower part thereof, contacted with a catalyst in the fluidized reactor 1 to carry out aromatics lightening reaction, a product rich in C6-C8 light aromatic(s) obtained after gas-solid separation is passed to a hot product gas-liquid separation tank 2 and a cold product gas-liquid separation tank 3 sequentially for carrying out gas-liquid separation to obtain recycle hydrogen 11 and a liquid product 10, the recycle hydrogen 11 is recycled after being treated to the fluidized reactor 1 for further reaction, the liquid product 10 is sent to an aromatics extraction unit 4 for aromatics extraction to obtain a non-aromatic component 12 and an aromatic component 13 by separation, the aromatic component 13 is sent to an aromatic separation column 5, C10+ aromatic component 15 obtained from the bottom of the column is mixed with the feedstocks 8 and then recycled to the fluidized reactor 1 for further reaction, C9 aromatic(s) 14 is obtained at a lower part of the aromatic separation column 5, BTEX (benzene, toluene, ethylbenzene and xylene) is obtained at the top of the column, the BTEX is sent to a product separation unit 6 for further separation to obtain benzene 18, toluene 16 and xylene 17, the C9 aromatic(s) 14 and the toluene 16 are mixed to obtain a mixed recycle feed 7, and the mixed recycle feed 7 is sent to the fluidized reactor 1 from a position downstream of the feeding position of the feedstock 8 for further reaction.

As shown in FIG. 2, in a further preferred embodiment, a feedstock 8 comprising heavy aromatic(s) and hydrogen 9 are fed to a fluidized reactor 1 from a lower part thereof to contact with a catalyst to carry out aromatics lightening reaction, the reaction product is sent to a gas-liquid separation tank 25 for carrying out gas-liquid separation to obtain a reaction liquid product 10 and hydrogen, the spent catalyst is continuously withdrawn from the fluidized reactor 1, passed through a reactor receiver 19 to a lock hopper 20, then to a regenerator feed tank 21, and then to a fluidized bed regenerator 22, and subjected to regeneration therein by coke burning in an oxygen-containing atmosphere, the resulted regenerated catalyst is continuously discharged to a regenerator receiver 23, then to a reducer 24 through the lock hopper 20 for reduction, and is continuously recycled to the fluidized reactor 1 for reuse.

In some preferred embodiments, the present application provides the following technical solutions:

Item 1, a method for producing light aromatics, comprising the steps of:
contacting a feedstock comprising heavy aromatic(s) with a catalyst in a fluidized reactor for lightening reaction in the presence of hydrogen to obtain a product rich in light aromatic(s) and a spent catalyst;
separating the product rich in light aromatic(s) to obtain hydrogen, a non-aromatic component, C6-C8 light aromatic(s) and a C9+ aromatic component, and recycling at least a part of the C9+ aromatic component to the fluidized reactor.

Item 2, the method of Item 1, wherein the lightening reaction is carried out under conditions including: a temperature of 250-750° C., a pressure of 0-6 MPa, a weight hourly space velocity of 0.1-7 $h^{-1}$, and a hydrogen/hydrocarbon molar ratio of 1-15; preferably, the lightening reaction is carried out under conditions including: a temperature of 320-600° C., a pressure of 0-4.5 MPa, a weight hourly space velocity of 1-6 $h^{-1}$, and a hydrogen/hydrocarbon molar ratio of 2-10; more preferably, the lightening reaction is carried out under conditions including: a temperature of 360-550° C., a pressure of 1-3 MPa, a weight hourly space velocity of 1.5-4.5 $h^{-1}$, and a hydrogen/hydrocarbon molar ratio of 3-8.

Item 3, the method of Item 1, wherein the separating comprises: subjecting the product rich in light aromatic(s) to gas-liquid separation to obtain hydrogen and a liquid product, and subjecting the liquid product to aromatics extraction to obtain the non-aromatic component and the aromatic component;
subjecting the aromatic component to a first fractionation to obtain the light aromatic(s) and the C9+ aromatic component; or alternatively, subjecting the aromatic component to a second fractionation to obtain the light aromatic(s), C9 aromatic(s), and a C10+ aromatic component.

Item 4, the method of Item 3, wherein the method further comprises: subjecting the light aromatic(s) to a third fractionation to obtain benzene, toluene and xylene, mixing the toluene and the C9 aromatic(s) to obtain a mixed recycle feed, and recycling the mixed recycle feed to the fluidized reactor; and mixing the C10+ aromatic component with the feedstock comprising heavy aromatic(s) and then recycling to the fluidized reactor for lightening reaction.

Item 5, the method of Item 4, wherein the C10+ aromatic component and the mixed recycle feed are fed to the fluidized reactor sequentially along a flow direction of the feedstock comprising heavy aromatic(s) within the fluidized reactor.

Item 6, the method of Item 1, wherein the method further comprises: recycling the hydrogen to the fluidized reactor for reuse.

Item 7, the method of Item 1, wherein the method further comprises: sending the spent catalyst to a fluidized bed regenerator for regeneration and recycling the resulted regenerated catalyst to the fluidized reactor.

Item 8, the method of Item 7, wherein the fluidized bed regenerator comprises a lock hopper, and the regeneration is carried out by: sending the spent catalyst to the fluidized bed regenerator for regeneration through the lock hopper, and recycling the regenerated catalyst to the fluidized reactor through the lock hopper.

Item 9, the method of Item 1, wherein the feedstock comprising heavy aromatic(s) has an initial boiling point of 120-150° C. and a final boiling point of 200-250° C.

Item 10, the method of Item 1, wherein the feedstock comprising heavy aromatic(s) has a C9+ aromatic(s) content of 20-100 wt %.

Item 11, the method of Item 1, wherein the feedstock is at least one selected from heavy aromatics derived from steam cracking gasoline, heavy aromatics derived from deep catalytic cracking gasoline, heavy aromatics derived from catalytic cracking gasoline, heavy aromatics derived from catalytic reforming and C9+ heavy aromatics from the bottom of xylene column in PX plant.

Item 12, the method of Item 1, wherein the fluidized reactor is a dilute-phase conveying bed reactor, a dense-phase fluidized bed reactor, a composite reactor composed of a dilute-phase conveying bed reactor and a dense-phase fluidized bed reactor, a composite reactor composed of two or more dilute-phase conveying bed reactors, or a composite reactor composed of two or more dense-phase fluidized bed reactors.

Item 13, the method of Item 12, wherein the dilute-phase conveying bed reactor is a riser reactor; and the dense-phase fluidized bed reactor is a bubbling fluidized bed reactor, a turbulent fluidized bed reactor or the like.

Item 14, the method of Item 1, wherein the fluidized reactor is a riser reactor or a downer reactor.

Item 15, the method of Item 1, wherein the catalyst comprises a carrier and an active metal component supported on the carrier in an amount of 0.01-50 wt % based on the total weight of the catalyst.

Item 16, the method of Item 15, wherein, based on the total weight of the carrier, the carrier comprises 1-60 wt % of zeolite, 5-99 wt % of inorganic oxide, and 0-70 wt % of clay;
wherein the zeolite comprises a mesoporous zeolite and/or a macroporous zeolite; the inorganic oxide is at least one of silica, alumina, zirconia, titania and amorphous silica-alumina; the clay is at least one selected from kaolin, montmorillonite, diatomite, attapulgite, sepiolite, halloysite, hydrotalcite, bentonite and rectorite.

Item 17, the method of Item 16, wherein the mesoporous zeolite is a ZSM zeolite and/or a ZRP zeolite and the macroporous zeolite is one or more selected from β zeolite, REY zeolite, REHY zeolite, ultrastable Y zeolite, and high silica Y zeolite.

Item 18, the method of Item 15, wherein the active metal component is one or a combination of two or more of rare earth metals and transition metals.

EXAMPLES

The present application will be further illustrated with reference to the following examples, but the present application is not limited thereto.

Carrier Preparation Example 1

Alumina sol (Qilu Branch of Sinopec Catalyst Co. ltd.) was divided into two parts with the same quantity, one part was mixed with kaolin (Qilu Branch of Sinopec Catalyst Co. ltd.), formed into slurry with a solid content of 40 wt % by using deionized water, uniformly stirred, the slurry was adjusted to a pH of 3.5 by using hydrochloric acid, maintained at the pH value, stood and aged at 60° C. for 1.5 hours, the rest of the alumina sol was added, stirred for 1.0 hour to form a colloid, a ZSM-5 molecular sieve (available from Qilu Branch of Sinopec Catalyst Co. ltd.) and a Y molecular sieve (available from Qilu Branch of Sinopec Catalyst Co. ltd.) were added to form a carrier slurry (with a solid content of 35 wt %), further stirred, and spray dried to obtain a microsphere carrier, wherein the weight ratio of ZSM-5 molecular sieve:Y molecular sieve:kaolin:aluminum sol=30:10:39:21.

The microsphere carrier was then calcined at 500° C. for 1 hour, washed with ammonium sulfate (ammonium sulfate: microsphere carrier:water=0.5:1:10) at 60° C. to a sodium oxide content of less than 0.25 wt. %, rinsed with deionized water and filtered, and then dried at 110° C. to obtain a carrier C1.

Carrier Preparation Example 2

Alumina sol was divided into two parts with the same quantity, one part was mixed with kaolin, formed into slurry with a solid content of 40 wt % by using deionized water, uniformly stirred, the slurry was adjusted to a pH of 3.5 by using hydrochloric acid, maintained at the pH value, stood and aged at 60° C. for 1.5 hours, the rest of the alumina sol was added, stirred for 1.0 hour to form a colloid, a Y molecular sieve was added to form a carrier slurry (with a solid content of 35 wt %), further stirred, and spray dried to obtain a microsphere carrier, wherein the weight ratio of Y molecular sieve:kaolin:aluminum sol=40:39:21.

The microsphere carrier was then calcined at 500° C. for 1 hour, washed with ammonium sulfate (ammonium sulfate: microsphere carrier:water=0.5:1:10) at 60° C. to a sodium oxide content of less than 0.25 wt. %, rinsed with deionized water and filtered, and then dried at 110° C. to obtain a carrier C2.

Catalyst Preparation Example 1

The carrier C1 was subjected to hydrothermal aging (800° C., 100% of steam, for 12 hours) and then added into a $PdCl_2$ solution for incipient wetness impregnation at an impregnation temperature of 80° C. for 120 min, dried for 2 hours at a temperature of 150° C., and then the carrier impregnated with Pd was added into a chloroplatinic acid solution for incipient wetness impregnation at an impregnation temperature of 80° C. for 120 min; the resultant was washed with deionized water, dried for 2 hours at a temperature of 150° C., calcined for 4 hours at a temperature of 500° C., and the calcined catalyst was reduced for 2 hours at a temperature of 100° C. in a hydrogen-containing gas, to obtain a catalyst H1 loaded with active metals Pd and Pt, wherein the loading amounts of Pd and Pt were respectively 0.04 wt % and 0.04 wt % (calculated on the basis of metal elements and relative to the total weight of the catalyst), the abrasion index was 3.2%/h, and the particle size distribution was as follows: the mass fraction of particles with a particle size of 0-20 μm was 3%, the mass fraction of particles with a particle size of 0-40 μm was 22%, the mass fraction of particles with a particle size of 0-149 μm was 89%, and the average particle size was 75 μm.

Catalyst Preparation Example 2

The carrier C1 was subjected to hydrothermal aging (800° C., 100% of steam, for 12 hours) and added into a $NiCl_2$ solution for incipient wetness impregnation at an impregnation temperature of 80° C. for 120 min, washed with deionized water, dried for 2 hours at 150° C., calcined for 4 hours at 500° C., and the calcined catalyst was subjected to presulfurization treatment to obtain a NiS-loaded catalyst H2, wherein the loading amount of NiS was 6.5% (calculated on the basis of Ni and relative to the total weight of the catalyst), the abrasion index was 3.2%/h, and the particle size distribution was as follows: the mass fraction of particles with a particle size of 0-20 μm was 3%, the mass fraction of particles with a particle size of 0-40 μm was 22%, the mass fraction of particles with a particle size of 0-149 μm was 89%, and the average particle size was 75 μm.

Catalyst Preparation Example 3

The carrier C2 was subjected to hydrothermal aging (800° C., 100% of steam, for 12 hours) and then added into a $PdCl_2$ solution for incipient wetness impregnation at an impregnation temperature of 80° C. for 120 min, dried at 150° C. for 2 hours, the carrier impregnated with Pd was then added into a chloroplatinic acid solution for incipient wetness impregnation at an impregnation temperature of 80° C. for 120 min, washed with deionized water, dried at 150° C. for 2 hours, calcined at 500° C. for 4 hours, the calcined catalyst was reduced in a hydrogen-containing gas at 100° C. for 2 hours to obtain a catalyst H3 loaded with active metals Pd and Pt, wherein the loading amounts of Pd and Pt were 0.04 wt % and 0.04 wt % respectively (calculated on the basis of metal elements and relative to the total weight of the catalyst), the abrasion index was 2.8%/h, and the particle size distribution was as follows: the mass fraction of particles with a particle size of 0-20 μm was 2.5%, the mass fraction of particles with a particle size of 0-40 μm was 19%, the mass fraction of particles with a particle size of 0-149 μm was 91%, and the average particle size was 73 μm.

Catalyst Preparation Example 4

The carrier C1 was subjected to hydrothermal aging (800° C., 100% of steam, for 12 hours) and then added into a $NiCl_2$ solution for incipient wetness impregnation at an impregnation temperature of 80° C. for 120 min, washed with deionized water, dried at 150° C. for 2 hours, calcined at 500° C. for 4 hours, and the calcined catalyst was reduced in a hydrogen-containing gas at 100° C. for 2 hours without presulfurization treatment to obtain a Ni-loaded catalyst H4, wherein the loading amount of Ni was 6.5% (calculated on the basis of Ni and relative to the total weight of the catalyst), the abrasion index was 3.2%/h, and the particle size distribution was as follows: the mass fraction of particles with a particle size of 0-20 μm was 3%, the mass fraction of particles with a particle size of 0-40 μm was 22%, the mass fraction of particles with a particle size of 0-149 μm was 89%, and the average particle size was 75 μm.

Catalyst Preparation Example 5

The carrier C1 was added, without subjecting to hydrothermal aging, into a $PdCl_2$ solution for incipient wetness impregnation at an impregnation temperature of 80° C. for 120 min, dried at a temperature of 150° C. for 2 hours, then the carrier impregnated with Pd was added into a chloroplatinic acid solution for incipient wetness impregnation at an impregnation temperature of 80° C. for 120 min, washed with deionized water, dried at a temperature of 150° C. for 2 hours, calcined at a temperature of 500° C. for 4 hours, the calcined catalyst was reduced in a hydrogen-containing gas at a temperature of 100° C. for 2 hours to obtain a catalyst H5 loaded with active metals Pd and Pt, wherein the loading amounts of Pd and Pt were 0.04 wt % and 0.04 wt % respectively (calculated on the basis of metal elements and relative to the total weight of the catalyst), the abrasion index was 3.2%/h, and the particle size distribution was as follows: the mass fraction of particles with a particle size of 0-20 μm was 2.5%, the mass fraction of particles with a particle size of 0-40 μm was 16%, the mass fraction of particles with a particle size of 0-149 μm was 87%, and the average particle size was 78 μm.

The following examples and comparative examples are provided illustrating the methods for producing light aromatics according to the present application and not according to the present application.

The properties of the heavy aromatics feedstock used are listed in Table 1, wherein feedstock A is heavy aromatics derived from deep catalytic cracking gasoline, feedstock B is heavy aromatics derived from steam cracking gasoline, and feedstock C is heavy aromatics derived from catalytic reforming.

TABLE 1

| Properties of heavy aromatics feedstock | | A | B | C |
|---|---|---|---|---|
| Density at 20° C./(kg/m³) | | 857.1 | 862.2 | 870.1 |
| Group composition/ | Parafins | 3.69 | 13.55 | 4.07 |
| % by mass | Naphthenes | 2.03 | 9.12 | 6.21 |
| | Olefins | 13.43 | 7.79 | 0.22 |
| | Aromatics | 80.85 | 69.54 | 89.50 |
| | $C_9$ aromatics | 58.95 | 47.90 | 66.94 |
| | $C_{10}^+$ aromatics | 19.52 | 11.89 | 22.56 |
| Distillation range/° C. | 5% | 162 | 146 | 159 |
| | 10% | 164 | 149 | 162 |
| | 30% | 170 | 156 | 170 |
| | 50% | 175 | 164 | 179 |
| | 70% | 181 | 169 | 187 |
| | 90% | 195 | 175 | 195 |
| | 95% | 205 | 181 | 198 |

In the results of each example and comparative example:
Conversion rate %=100%−the total content by mass expressed in percentage of all components in the product that are the same as those in the feedstock;
BTX selectivity=BTX yield/conversion rate;
Xylene selectivity=xylene yield/conversion rate.

Example 1

The experiment was carried out in accordance with the flow scheme shown in FIGS. 1 and 2, on a pilot dense-phase fluidized bed reactor with continuous regeneration using feedstock A and catalyst H1. Relevant conditions and products are listed in Table 2.

Example 2

The experiment was carried out as described in Example 1, except that the reaction temperature was 480° C. Relevant conditions and products are listed in Table 2.

Example 3

The experiment was carried out as described in Example 1, except that catalyst H2 was used. Relevant conditions and products are listed in Table 2.

Example 4

The experiment was carried out as described in Example 1, except that catalyst H3 was used. Relevant conditions and products are listed in Table 2.

Example 5

The experiment was carried out as described in Example 1, except that feedstock B was used. Relevant conditions and products are listed in Table 2.

Example 6

The experiment was carried out as described in Example 1, except that feedstock C was used. Relevant conditions and products are listed in Table 2.

TABLE 2

| Conditions and products of Examples 1-6 | | | | | | |
|---|---|---|---|---|---|---|
| | Ex. 1 | Ex. 2 | Ex. 3 | Ex. 4 | Ex. 5 | Ex. 6 |
| Feedstock | A | A | A | A | B | C |
| Catalyst | H1 | H1 | H2 | H3 | H1 | H1 |
| Reactor type | Dense-phase fluidized bed | Dense-phase fluidized bed | Dense-phase fluidized bed | Dense-phase fluidized bed | Dense-phase fluidized bed | Dense-phase fluidized bed |
| Reaction conditions | | | | | | |
| Reaction temperature/° C. | 450 | 480 | 450 | 460 | 450 | 450 |
| Pressure/MPa | 1 | 1 | 1 | 1 | 1 | 1 |
| Space velocity/h$^{-1}$ | 2 | 2 | 2 | 2 | 2 | 2 |
| Hydrogen/hydrocarbon molar ratio | 3 | 3 | 3 | 3 | 3 | 3 |

TABLE 2-continued

Conditions and products of Examples 1-6

|  |  | Ex. 1 | Ex. 2 | Ex. 3 | Ex. 4 | Ex. 5 | Ex. 6 |
|---|---|---|---|---|---|---|---|
|  | Recycle mode for C9 aromatics and toluene | Mixed recycle | Mixed recycle | Mixed recycle | Mixed recycle | Mixed recycle | Mixed recycle |
| Yield of products/% | Gas(es) | 11.21 | 13.45 | 12.02 | 13.17 | 13.98 | 10.87 |
|  | Gasoline | 83.86 | 81.40 | 83.52 | 82.91 | 82.02 | 84.71 |
|  | Benzene | 6.69 | 6.79 | 6.38 | 5.08 | 4.78 | 7.46 |
|  | Toluene | 4.81 | 5.41 | 4.78 | 3.10 | 2.81 | 5.21 |
|  | Xylene | 37.26 | 38.16 | 37.15 | 36.26 | 35.55 | 38.87 |
|  | C9 aromatics | 17.42 | 16.51 | 17.49 | 17.53 | 14.40 | 20.21 |
|  | C10+ aromatics | 5.81 | 5.37 | 5.96 | 5.36 | 4.93 | 6.47 |
|  | Conversion rate/% | 73.77 | 76.12 | 73.91 | 72.68 | 72.45 | 76.82 |
|  | BTX selectivity/% | 66.10 | 66.16 | 65.36 | 61.14 | 59.54 | 67.09 |
|  | Xylene selectivity/% | 50.51 | 50.13 | 50.26 | 49.89 | 49.07 | 50.60 |

The product yield refers to the weight ratio of the corresponding product to the total amount of the feedstock.

Example 7

The experiment was carried out as described in Example 1, except that the separated C9 aromatics were not mixed with toluene, but were fed separately into the reactor for reaction at a place downstream of the feeding nozzle, and the toluene was not recycled but directly withdrawn as a product. Relevant conditions and products are listed in Table 3.

Example 8

The experiment was carried out as described in Example 1, except the different reaction conditions in the dense-phase fluidized bed reactor were employed. Relevant conditions and products are listed in Table 3.

Example 9

The experiment was carried out as described in Example 1, except that catalyst H4 was used. Relevant conditions and products are listed in Table 3.

Example 10

The experiment was carried out as described in Example 1, except that catalyst H5 was used. Relevant conditions and products are listed in Table 3.

Example 11

The experiment was carried out as described in Example 1, except that a riser reactor was used as the reactor. Relevant conditions and products are listed in Table 3.

Example 12

The experiment was carried out as described in Example 1, except that a composite reaction of a riser reactor and a dense-phase fluidized bed reactor was used as the reactor. Relevant conditions and products are listed in Table 3.

TABLE 3

Conditions and results for Examples 7-12

|  |  | Ex. 7 | Ex. 8 | Ex. 9 | Ex. 10 | Ex. 11 | Ex. 12 |
|---|---|---|---|---|---|---|---|
|  | Feedstock | A | A | A | A | A | A |
|  | Catalyst | H1 | H1 | H4 | H5 | H1 | H1 |
|  | Reactor type | Dense-phase fluidized bed | Dense-phase fluidized bed | Dense-phase fluidized bed | Dense-phase fluidized bed | Riser reactor | Riser reactor plus dense-phase fluidized bed |
| Reaction conditions | Reaction temperature/° C. | 450 | 450 | 450 | 450 | 450 | 450 |
|  | Pressure/MPa | 1 | 3 | 1 | 1 | 1 | 1 |
|  | Space velocity/h$^{-1}$ | 2 | 1 | 2 | 2 | Reaction time 2 s | Riser reactor reaction time 2 s/ fluidized bed space velocity 6 |
|  | Hydrogen/hydrocarbon molar ratio | 3 | 4 | 3 | 3 | 3 | 3 |
|  | Recycle mode for C9 aromatics and toluene | Toluene was not recycled | Mixed recycle | Mixed recycle | Mixed recycle | Mixed recycle | Mixed recycle |
| Yield of products/% | Gas(es) | 11.31 | 18.81 | 10.12 | 17.33 | 9.72 | 10.23 |
|  | Gasoline | 84.01 | 76.98 | 85.57 | 80.06 | 85.45 | 85.10 |
|  | Benzene | 4.56 | 5.22 | 6.56 | 6.86 | 6.44 | 6.56 |
|  | Toluene | 13.40 | 3.34 | 5.12 | 4.69 | 5.09 | 4.93 |
|  | Xylene | 16.54 | 33.78 | 38.02 | 37.55 | 37.96 | 37.77 |
|  | C9 aromatics | 26.66 | 18.64 | 17.81 | 17.63 | 17.67 | 17.52 |
|  | C10+ aromatics | 8.75 | 6.48 | 6.12 | 5.94 | 6.15 | 6.02 |
|  | Conversion rate/% | 59.81 | 71.98 | 73.83 | 76.52 | 73.01 | 73.42 |

TABLE 3-continued

Conditions and results for Examples 7-12

|  | Ex. 7 | Ex. 8 | Ex. 9 | Ex. 10 | Ex. 11 | Ex. 12 |
|---|---|---|---|---|---|---|
| BTX selectivity/% | 57.68 | 58.82 | 67.32 | 64.17 | 67.79 | 67.09 |
| Xylene selectivity/% | 27.65 | 46.93 | 51.50 | 49.07 | 51.99 | 51.44 |

Comparative Example 1

The experiment was carried out as described in Example 1, except that toluene and C9+ heavy aromatics separated from the product were not recycled to the reactor. Relevant conditions and products are listed in Table 4.

Comparative Example 2

The experiment was carried out as described in Example 1, except that a fixed bed reactor was used as the reactor, no additional equipment was used for separating the catalyst and the oil gas, and the catalyst was not continuously regenerated. Relevant conditions and products are listed in Table 4.

Comparative Example 3

The experiment was carried out as described in Example 1, except that the reaction was carried out in the absent of hydrogen using hydrothermally aged carrier C2 as a catalyst. Relevant conditions and products are listed in Table 4.

TABLE 4

Conditions and results of Comparative Examples 1-3

|  |  | Comp. Ex. 1 | Comp. Ex. 2 | Comp. Ex. 3 |
|---|---|---|---|---|
|  | Feedstock | A | A | A |
|  | Catalyst | H1 | H1 | C2 |
|  | Reactor type | Dense-phase fluidized bed | Fixed bed | Dense-phase fluidized bed |
| Reaction conditions | Reaction temperature/° C. | 450 | 450 | 580 |
|  | Pressure/MPa | 1 | 1 | Atmospheric pressure |
|  | Space velocity/h$^{-1}$ | 2 | 2 | 6 |
|  | Hydrogen/hydrocarbon molar ratio | 3 | 3 | — |
|  | Recycle mode for C9 aromatics and toluene | Toluene and C9+ aromatics were not recycled | Mixed recycle | Mixed recycle |
| Yield of products/% | Gas(es) | 11.45 | 23.79 | 14.89 |
|  | Gasoline | 83.59 | 72.35 | 73.45 |
|  | Benzene | 3.65 | 3.29 | 3.16 |
|  | Toluene | 11.99 | 2.11 | 5.30 |
|  | Xylene | 14.42 | 27.16 | 17.04 |
|  | C9 aromatics | 30.17 | 24.47 | 30.95 |
|  | C10+ aromatics | 10.05 | 8.56 | 7.19 |
|  | Conversion rate/% | 53.10 | 65.91 | 54.95 |
|  | BTX selectivity/% | 56.61 | 49.40 | 46.41 |
|  | Xylene selectivity/% | 27.16 | 41.21 | 31.01 |

As can be seen from the results of the above examples and comparative examples, the method for producing light aromatics of the present application can produce light aromatics from various heavy aromatic feedstocks, and shows high feedstock conversion and BTX selectivity; the method can further improve the xylene selectivity by recycling the C9 aromatic(s) and the toluene, and has great flexibility in operation, and allows a long-period stable operation, in which the catalyst is easy to be regenerated, and the mass and heat transfer is uniform.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A method for producing light aromatics, comprising the steps of:
   i) contacting a feedstock with a catalyst in a fluidized reactor for aromatics lightening reaction in the presence of hydrogen to obtain a product rich in C6-C8 light aromatics and a spent catalyst, wherein the feedstock comprises heavy aromatics that is one or more selected from C9+ aromatics;
   ii) separating the product rich in C6-C8 light aromatics to obtain hydrogen, a non-aromatic component, C6-C8 light aromatics and a C9+ aromatic component; and
   iii) recycling at least a part of the C9+ aromatic component to the fluidized reactor,
   wherein:
   the reaction conditions of step i) include: a temperature of about 250-750° C., a pressure of about 0-6 MPa, a weight hourly space velocity of about 0.1-120 h$^{-1}$ or a reaction time of about 0.1-40 seconds, and a hydrogen/hydrocarbon molar ratio of about 1-15, wherein the pressure is a gauge pressure,
   the catalyst in step i) comprises a carrier and an active metal component supported on the carrier in an amount of about 0.01-50 wt %, based on the total weight of the catalyst,
   wherein the carrier comprises from about 1 wt % to about 80 wt % of zeolite, from about 5 wt % to about 99 wt % of inorganic oxide, and from about 0 wt % to about 70 wt % of clay, based on the total weight of the carrier,
   wherein the zeolite comprises a mesoporous zeolite, a macroporous zeolite, or a combination thereof; the inorganic oxide is one or more selected from silica, alumina, zirconia, titania, and amorphous silica-alumina; the clay is one or more selected from kaolin, montmorillonite, diatomite, attapulgite, sepiolite, halloysite, hydrotalcite, bentonite, and rectorite, the active metal component is one or more selected from rare earth metals and transition metals, wherein the separation of step ii) further comprises the steps of:

subjecting the product rich in C6-C8 light aromatics to gas-liquid separation to obtain hydrogen and a liquid product;

subjecting the liquid product to aromatics extraction to obtain a non-aromatic component and an aromatic component; and subjecting the aromatic component to a first fractionation to obtain C6-C8 light aromatics and a C9+ aromatic component, or subjecting the aromatic component to a second fractionation to obtain C6-C8 light aromatics, C9 aromatics, and a C10+ aromatic component.

2. The method according to claim 1, wherein the reaction conditions of step i) include: a temperature of about 320-600° C., a pressure of about 0-4.5 MPa, a weight hourly space velocity of about 1-80 h$^{-1}$ or a reaction time of about 0.5-30 seconds, and a hydrogen/hydrocarbon molar ratio of about 2-10.

3. The method according to claim 1, wherein after said step ii), the method further comprises one or more steps selected from:

subjecting the C6-C8 light aromatics to a third fractionation to obtain benzene, toluene and xylene;

mixing the toluene and the C9 aromatics to obtain a mixed recycle feed, and recycling the mixed recycle feed to the fluidized reactor; and mixing the C10+ aromatic component with the feedstock and recycling the resulting mixture to the fluidized reactor.

4. The method according to claim 3, wherein the mixed recycle feed is recycled to the fluidized reactor at a position downstream of the position at which the resulting mixture containing the C10+ aromatic component is recycled, along the flow direction of the feedstock within the fluidized reactor.

5. The method according to claim 1, further comprising the step of:

regenerating the spent catalyst in a fluidized bed regenerator and recycling the regenerated catalyst to the fluidized reactor.

6. The method according to claim 5, wherein the fluidized bed regenerator comprises a lock hopper, and the regeneration is carried out by:

sending the spent catalyst to the fluidized bed regenerator for regeneration through the lock hopper, and recycling the regenerated catalyst to the fluidized reactor through the lock hopper.

7. The method according to claim 6, further comprising the step of depressurizing the spent catalyst in the lock hopper and the step of pressurizing the regenerated catalyst in the lock hopper.

8. The method according to claim 6, wherein the fluidized bed regenerator further comprises a reactor receiver, a regenerator receiver, a regenerator feed tank, and optionally a reducer, and the regeneration is carried out by:

sending the spent catalyst from the fluidized reactor to the reactor receiver, then to the regenerator feed tank through the lock hopper, and then from the regenerator feed tank to the fluidized bed regenerator;

subjecting the spent catalyst to regeneration by coke-burning in the regenerator under an oxygen-containing atmosphere to obtain the regenerated catalyst; and recycling the regenerated catalyst from the fluidized bed regenerator, to the fluidized reactor for reuse directly through the regenerator receiver, or to the fluidized reactor for reuse after being reduced in a reducer.

9. The method according to claim 1, wherein the feedstock has an initial boiling point of about 120° C. to about 150° C. and a final boiling point of about 200° C. to about 250° C.

10. The method according to claim 1, wherein the feedstock is at least one selected from heavy aromatics derived from steam cracking gasoline, heavy aromatics derived from deep catalytic cracking gasoline, heavy aromatics derived from catalytic cracking gasoline, and heavy aromatics derived from catalytic reforming and C9+ heavy aromatics from a bottom of xylene column in aromatics complex plant.

11. The method according to claim 1, wherein the fluidized reactor is selected from a conveying bed reactor, a dense-phase fluidized bed reactor, a composite reactor composed of a conveying bed reactor and a dense-phase fluidized bed reactor, a composite reactor composed of two or more conveying bed reactors, and a composite reactor composed of two or more dense-phase fluidized bed reactors.

12. The method according to claim 11, wherein the conveying bed reactor is a riser reactor; and the dense-phase fluidized bed reactor is a bubbling fluidized bed reactor or a turbulent fluidized bed reactor.

13. The method according to claim 1, wherein the mesoporous zeolite is one or more selected from ZSM zeolites and ZRP zeolites, and the macroporous zeolite is one or more selected from ß zeolites, REY zeolites, REHY zeolites, ultrastable Y zeolites, and high silica Y zeolites.

14. The method according to claim 1, wherein the mesoporous zeolite is present in an amount of from about 0 wt % to about 100 wt %, and the macroporous zeolite is present in an amount of from about 0 wt % to about 100 wt %, based on the total weight of the zeolite.

15. The method according to claim 14, wherein the mesoporous zeolite is present in an amount of from about 50 wt % to about 100 wt %.

16. The method according to claim 14, wherein the mesoporous zeolite is present in an amount of from about 70 wt % to about 90 wt %.

17. The method according to claim 14, wherein the macroporous zeolite is present in an amount of from about 0 wt % to about 50 wt %.

18. The method according to claim 14, wherein the macroporous zeolite is present in an amount of from about 10 wt % to about 30 wt %.

19. The method according to claim 1, wherein the reaction conditions of step i) include: a temperature of about 360-550° C., a pressure of about 1-3 MPa, a weight hourly space velocity of about 1.5-50 h$^{-1}$ or a reaction time of about 1-15 seconds, and a hydrogen/hydrocarbon molar ratio of about 3-8.

20. The method according to claim 1, wherein the feedstock has a total content of C9+ aromatics of about 20 wt. % to about 100 wt. %.

* * * * *